US00PP20702P2

(12) United States Plant Patent
Hosogai

(10) Patent No.: US PP20,702 P2
(45) Date of Patent: Feb. 2, 2010

(54) ***COREOPSIS* PLANT NAMED 'SWEET MARMALADE'**

(50) Latin Name: *Coreopsis verticillata*
Varietal Denomination: Sweet Marmalade

(75) Inventor: Yohei Hosogai, Akiba-ku Niigata (JP)

(73) Assignee: June Croon, Cutchogue, NY (US)

( * ) Notice: Subject to any disclaimer, the term of this patent is extended or adjusted under 35 U.S.C. 154(b) by 0 days.

(21) Appl. No.: 12/228,290

(22) Filed: Aug. 11, 2008

(51) Int. Cl.
*A01H 5/00* (2006.01)

(52) U.S. Cl. ..... Plt./417
(58) Field of Classification Search ..... Plt./417
See application file for complete search history.

*Primary Examiner*—June Hwu
(74) *Attorney, Agent, or Firm*—C. A. Whealy

(57) ABSTRACT

A new and distinct cultivar of *Coreopsis* plant named 'Sweet Marmalade', characterized by its upright, outwardly spreading and mounded plant habit; vigorous growth habit; freely branching habit; freely flowering habit with numerous inflorescences per plant; daisy-type inflorescences with yellow to light orange-colored ray florets; relatively resistant to Powdery Mildew; and good garden performance.

1 Drawing Sheet

Botanical designation: *Coreopsis verticillata.*
Cultivar denomination: 'Sweet Marmalade'.

BACKGROUND OF THE INVENTION

The present invention relates to a new and distinct cultivar of *Coreopsis* plant, botanically known as *Coreopsis verticillata*, and hereinafter referred to by the name 'Sweet Marmalade'.

The new *Coreopsis* plant is a naturally-occurring whole plant mutation of *Coreopsis verticillata* 'Creme Brulee', disclosed in U.S. Plant Pat. No. 16,096. The new *Coreopsis* plant was discovered and selected by the Inventor as a single flowering plant within a population of plants of 'Creme Brulee' in a controlled outdoor nursery environment in Niitsu City, Niigata, Japan in July, 2006.

Asexual reproduction of the new *Coreopsis* plant by vegetative cuttings in a controlled environment in Niitsu City, Niigata, Japan since September, 2006, has shown that the unique features of this new *Coreopsis* plant are stable and reproduced true to type in successive generations.

SUMMARY OF THE INVENTION

Plants of the new *Coreopsis* have not been observed under all possible environmental conditions. The phenotype may vary somewhat with variations in environment such as temperature and light intensity, without, however, any variance in genotype.

The following traits have been repeatedly observed and are determined to be the unique characteristics of 'Sweet Marmalade'. These characteristics in combination distinguish 'Sweet Marmalade' as a new and distinct cultivar of *Coreopsis:*

1. Upright, outwardly spreading and mounded plant habit.
2. Vigorous growth habit.
3. Freely branching habit.
4. Freely flowering habit with numerous inflorescences per plant.
5. Daisy-type inflorescences with yellow to light orange-colored ray florets.
6. Relatively resistant to Powdery Mildew.
7. Good garden performance.

Plants of the new *Coreopsis* differ from plants of 'Creme Brulee' primarily in ray floret coloration as plants of 'Creme Brulee' have bright yellow-colored ray florets.

Plants of the new *Coreopsis* can be compared to *Coreopsis* 'Moonbeam', not patented. Plants of the new *Coreopsis* differ from plants of 'Moonbeam' in the following characteristics:

1. Plants of the new *Coreopsis* are more vigorous than plants of 'Moonbeam'.
2. Plants of the new *Coreopsis* have brighter green-colored leaves than plants of 'Moonbeam'.
3. Plants of the new *Coreopsis* have larger inflorescences than plants of 'Moonbeam'.
4. Plants of the new *Coreopsis* and 'Moonbeam' differ in ray floret color as plants of 'Moonbeam' have light yellow-colored ray florets.
5. Plants of the new *Coreopsis* are more resistant to Powdery Mildew than plants of the cultivar Moonbeam.

BRIEF DESCRIPTION OF THE PHOTOGRAPHS

The accompanying photographs illustrate the overall appearance of the new *Coreopsis* plant. The photographs show the colors as true as it is reasonably possible to obtain in colored reproductions of this type. Colors in the photographs may differ slightly from the color values cited in the detailed botanical description which accurately describe the colors of the new *Coreopsis* plant.

The photograph at the bottom of the sheet comprises a side perspective view of a typical flowering plant of 'Sweet Marmalade' grown in a container.

The photograph at the top of the sheet is a close-up view of typical inflorescences of 'Sweet Marmalade'.

DETAILED BOTANICAL DESCRIPTION

The aforementioned photographs and following observations and measurements describe plants grown one-gallon containers in Lancaster, Pa. during the spring in a polyethylene-covered greenhouse and under conditions and practices which approximate those generally used in commercial *Coreopsis* production. During the production of the plants, day temperatures ranged from 18° C. to 27° C. and night temperatures ranged from 13° C. to 18° C. Plants were pinched one time and had been growing for six months when the photographs and description. In the following description, color references are made to The Royal Horticultural Society Colour Chart, 2007 Edition, except where general terms of ordinary dictionary significance are used. Measurements represent averages for typical flowering plants.

Botanical classification: *Coreopsis verticillata* 'Sweet Marmalade'.

Parentage: Naturally-occurring whole plant mutation of *Coreopsis verticillata* 'Creme Brulee', disclosed in U.S. Plant Pat. No. 16,096.

Propagation:

*Type.*—By vegetative cuttings.

*Time to initiate roots.*—About one week at 25° C.

*Time to produce a rooted young plant.*—About one month at 25° C.

*Root description.*—Thin, fibrous.

*Rooting habit.*—Freely branching; dense.

Plant description:

*Plant form/growth habit.*—Upright, outwardly spreading and mounding plant habit; inverted triangle; freely branching habit with about 22 lateral branches. Vigorous growth habit.

*Plant height.*—About 52 cm.

*Plant diameter or spread: About* 48 cm.

*Lateral branches.*—Length: About 32 cm. Diameter: About 2 mm. Internode length: About 5.5 cm. Aspect: Mostly upright to outwardly spreading. Strength: Strong, flexible. Texture: Sparsely pubescent. Color: Close to 146B.

Foliage description:

*Arrangement.*—Opposite, simple.

*Length.*—About 4.5 cm.

*Width, with lobes.*—About 2.8 cm.

*Shape.*—Three to five-lobed; deeply dissected.

*Apex.*—Acute.

*Base.*—Attenuate.

*Margin.*—Entire, deeply incised.

*Texture, upper and lower surfaces.*—Pubescent.

*Venation pattern.*—Pinnate.

*Color.*—Developing leaves, upper surface: Close to N137B. Developing leaves, lower surface: Close to 137B. Fully expanded leaves, upper surface: Close to N137C; venation, close to 146B. Fully expanded leaves, lower surface: Close to 146B; venation, close to 146B.

*Petioles.*—Length: About 3.2 cm. Diameter: About 1 mm. Texture, upper surface: Sparsely pubescent. Texture, lower surface: Smooth, glabrous. Color, upper surface: Close to 146B. Color, lower surface: Close to 146C.

Inflorescence description:

*Appearance.*—Daisy-type (single) terminal and axillary inflorescences with ray and disc florets arranged acropetally on a capitulum. Inflorescences positioned above and beyond the foliage on moderately strong peduncles; inflorescences face mostly upright.

*Flowering habit.*—Freely flowering habit; about 40 inflorescences developing per lateral branch.

*Fragrance.*—None detected.

*Time to flower.*—Under natural season conditions, plants flower from June through July in Lancaster, Pa.; inflorescences persistent.

*Post-production longevity.*—Inflorescences maintain good substance for about three to five days on the plant.

*Inflorescence bud.*—Height: About 8 mm. Diameter: About 7 mm. Shape: Initially rounded becoming ovoid with development. Color: Close to 9B.

*Inflorescence size.*—Diameter: About 3.2 cm. Depth (height): About 1 cm. Disc diameter: About 8 mm. Receptacle height: About 6 mm. Receptacle diameter: About 8 mm. Receptacle color: Close to 137C.

*Ray florets.*—Length: About 1.8 cm. Width: About 8 mm. Shape: Obovate. Apex: Emarginate; ragged appearance. Base: Attenuate. Texture, upper and lower surfaces: Smooth, glabrous; slightly longitudinally ridged. Number of ray florets per inflorescence: About eight arranged in a single whorl. Aspect: Flat; perpendicular to peduncle. Color: When opening, upper surface: Close to 7A. When opening, lower surface: Close to 7B. Fully developed, upper surface: Ground color, close to 9A; mid-section and towards the apex, overlain with close to 163B. With development, overlain color becomes closer to 163A. Fully developed, lower surface: Close to 9B.

*Disc florets.*—Shape: Tubular, slender; apex dentate. Length: About 8 mm. Diameter: About 1.5 mm. Number of disc florets per inflorescence: About 160. Color, immature: Apex: Close to 153B. Mid-section: Close to 165B. Base: Close to 150C. Color, mature: Apex: Close to 153D. Mid-section: Close to 153A. Base: Close to 150C.

*Phyllaries.*—Quantity per inflorescence: About 16 in two whorls. Length, outer whorl: About 8 mm. Length, inner whorl: About 4 mm. Width, outer whorl: About 3 mm. Width, inner whorl: About 2 mm. Shape: Elliptical. Apex: Acute. Base: Truncate. Margin: Entire. Texture, upper and lower surfaces: Smooth, glabrous. Color, upper and lower surfaces: Close to 146C.

*Peduncles.*—Length: About 6.7 cm. Diameter: About 1 mm. Strength: Moderately strong. Aspect: Mostly upright to about 20° to 30° from vertical. Texture: Smooth, glabrous. Color: Close to 146B.

*Reproductive organs.*—Androecium (present on disc florets only): Quantity per disc floret: Five. Filament length: About 2.5 cm. Filament color: Close to 145C. Anther shape: Oblong, slender. Anther length: About 2 mm. Anther color: Close to 165B. Pollen amount: Scarce. Pollen color: Close to 21A. Gynoecium (present on disc florets only): Quantity per floret: One. Pistil length: About 8 mm. Stigma shape: Bi-parted. Stigma color: Close to 17A. Style length: About 4 mm. Style color: Close to 150C. Ovary color: Close to 157D.

*Seed/fruit.*—Seed and fruit production has not been observed.

Disease/pest resistance: Plants of the new *Coreopsis* have been shown to be relatively resistant to Powdery Mildew. Plants of the new *Coreopsis* have not been shown to be resistant to pests and other pathogens common to *Coreopsis*.

Garden performance: Plants of the new *Coreopsis* have exhibited good tolerance to rain and wind and have been observed to tolerate temperatures from about −10° C. to about 40° C.

It is claimed:

1. A new and distinct *Coreopsis* plant named 'Sweet Marmalade' as illustrated and described.

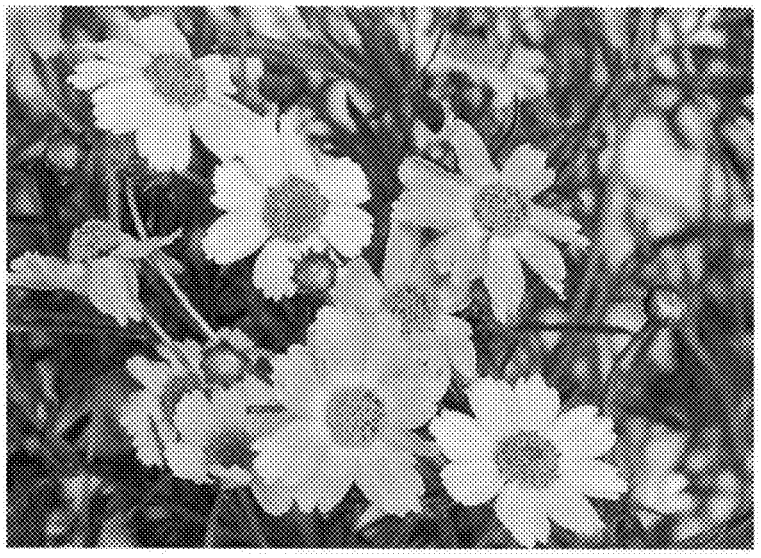
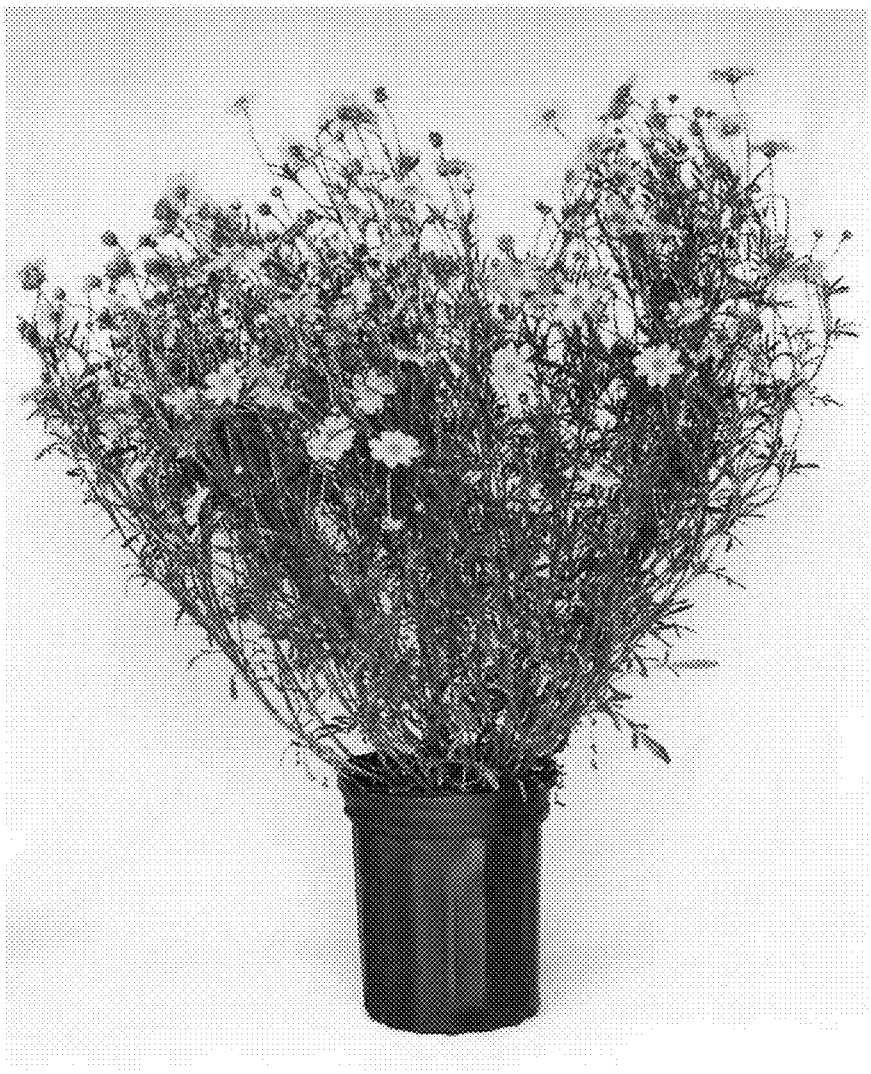

* * * * *